United States Patent [19]

Keith et al.

[11] Patent Number: 4,466,953

[45] Date of Patent: Aug. 21, 1984

[54] POLYMERIC DIFFUSION MATRIX

[75] Inventors: Alec D. Keith; Wallace Snipes, both of State College, Pa.

[73] Assignee: Key Pharmaceuticals, Inc., Miami, Fla.

[21] Appl. No.: 431,735

[22] Filed: Sep. 30, 1982

Related U.S. Application Data

[63] Continuation of Ser. No. 258,456, Apr. 28, 1981, which is a continuation of Ser. No. 109,242, Jan. 3, 1980, abandoned, which is a continuation-in-part of Ser. No. 47,084, Jun. 11, 1979, abandoned, which is a continuation-in-part of Ser. No. 2,565, Jan. 11, 1979, abandoned.

[30] Foreign Application Priority Data

Aug. 14, 1979 [JP] Japan ............................ 54-103495

[51] Int. Cl.³ ..................... A61K 9/70; A61L 15/03
[52] U.S. Cl. .................................. 424/28; 424/22; 424/78
[58] Field of Search .................. 424/28, 78, 80, 22

[56] References Cited

U.S. PATENT DOCUMENTS

| | | | |
|---|---|---|---|
| 2,127,896 | 10/1938 | Vohrer | 18/55 |
| 2,138,751 | 11/1938 | Vohrer | 18/54 |
| 2,155,658 | 4/1939 | Herrmann et al. | 424/78 |
| 2,160,503 | 5/1939 | Herrmann | 424/78 |
| 2,340,866 | 2/1944 | Dangelmajer | 260/8 |
| 2,491,642 | 12/1949 | Brant | 264/213 |
| 2,693,438 | 11/1954 | Ward | 424/28 |
| 3,287,222 | 11/1966 | Larde et al. | 424/28 |
| 4,210,633 | 7/1980 | Takruri et al. | 424/28 |

FOREIGN PATENT DOCUMENTS

| | | |
|---|---|---|
| 1505318 | 12/1967 | France . |
| 2245161 | 4/1975 | France . |
| 7392522 | 11/1973 | Japan . |
| 74-30525 | 3/1974 | Japan . |
| 7445952 | 5/1974 | Japan . |
| 7448728 | 12/1974 | Japan . |
| 76112511 | 3/1975 | Japan . |
| 7556385 | 5/1975 | Japan . |
| 7738016 | 3/1977 | Japan . |
| 7850320 | 5/1978 | Japan . |
| 933668 | 8/1963 | United Kingdom ............ 424/78 |
| 1108837 | 4/1968 | United Kingdom . |
| 219116 | 3/1973 | U.S.S.R. . |

OTHER PUBLICATIONS

Riegelman, Clin. Pharm. & Therapeutics, 16, (Part 2): 873-883, (1974), "Pharmacokinetics Factors Affecting Epidermal Penetration and Percutaneous Absorption".
Brooker et al., C.A. 84: 1557070, (1976), Topical Veterinary Sedative Ger. Off., 2537203, Fisions, C.A. 90:612Y9T, (1979), (Belg. 865088).
Van Dam, C.A. 55: 9674i-9675a, (1961), Current Concepts in Therapy New Engl., J. Med., 263:748-750, 963-965, (1960).
Goldblum et al., C.A. 49:507a, (1955), Barbiturate Concentrations in Skin.
Loth, C.A. 93:155742n, (1980), Gordean Knots of Biopharmaceutics.
Dtsh. Apoth-2tg., (19800, 120(19):846-852, (Ger.), (Phenobarbitol-Skin Drug Delivery).
Peierls Modern Plastics, 18:53-56, Feb. 1941, Polyvinyl Alcohol Plastics.
Hess et al., Rubber Age, 53:431-433, Aug. 1943, Molding Polyvinyl Alcohol.
Ita et al., Bulletin Pharm. Research Inst., Osaka Medical College, (2) 1-3, (1951), II, "On a New Water-Soluble Ointment".
(List continued on next page.)

Primary Examiner—Shep K. Rose
Attorney, Agent, or Firm—Wegner & Bretschneider

[57] ABSTRACT

A polymeric diffusion matrix is provided comprising from about 2 to about 60% glycerol, from about 2 to about 15% polyvinylalcohol, from about 2 to about 10% water soluble polymer with hydration sites which in combination with the remaining ingredients yields a matrix capable of sustained release of a drug dispersed therein, and the balance water, the percentages being by weight.

9 Claims, 2 Drawing Figures

OTHER PUBLICATIONS

Hirai Bull. Inst. Chem. Koyoto Univ., 33: 21–37, (1955), The Gel–Elasticity of High Polymers.

Langhammer et al., Naturwissen Schaften, 43: 125–126, (1956), (PVP–PVA).

(PVP—PVA) Nehring Plaste und Kautschuk, 3: 277–280, (1956).

Ward et al., Amer. Perf. & Cosmetics, 79:53–55, Nov. 1964, The Use of Polyvinyl Alcohol in Film-Forming Bases.

Ward et al., J. Soc. Cos. Chem., 15:327–335, (1964), Cosmetic Applications of Polyvinyl Alcohol.

Toyoshima, K., "Compatibility of Polyvinyl Alcohol with Other Water-Soluble High Polymers" in Finch et al., ED (1967), Polyvinyl Alcohol: Properties & Applications, 535–553.

Ban et al., Pharmazie, 29 H9:597–602, (1974), (PVP-PVA).

Nagy et al., "Formation of Disperse Structures in Polymer Gels", Proc. Int. Conf. Colloid & Surface Science, Budapest, Hungary, Sep. 1975, Wolfram ed., pp. 447–453.

POLYMERIC DIFFUSION MATRIX

CROSS-REFERENCE TO RELATED APPLICATIONS

This application is a continuation of application Ser. No. 258,456, filed Apr. 28, 1981, which in turn is a continuation of application Ser. No. 109,242, filed Jan. 3, 1980 and now abandoned, which in turn is a continuation-in-part of application Ser. No. 47,084, filed June 11, 1979 and now abandoned, which in turn is a continuation-in-part of application Ser. No. 2,565 filed Jan. 11, 1979 now abandoned.

SUMMARY OF THE INVENTION

A polymeric diffusion matrix is provided comprising from about 2 to about 60% glycerol, from about 2 to about 15% polyvinylalcohol, from about 2 to about 10% water soluble polymer with hydration sites which in combination with the remaining ingredients yields a matrix capable of sustained release of a drug dispersed therein, and the balance water, the percentages being by weight. Preferably, said water soluble polymer is polyvinylpyrrolidone, agar, agarose or a water soluble cellulose derivative, a preferred embodiment being polyvinylpyrrolidone. The polyvinylalcohol preferably has a molecular weight of from about 100,000 to about 150,000 and the polyvinylpyrrolidone preferably has a molecular weight of from about 20,000 to about 60,000.

In a preferred embodiment, a polymeric diffusion matrix suitable for the transdermal delivery of a drug is provided comprising from about 2 to about 60% glycerol, from about 2 to about 15% polyvinylalcohol, from about 2 to about 10% water soluble polymer with hydration sites which in combination with the remaining ingredients yields a matrix capable of sustained release of a drug dispersed therein, at least one drug suitable for transdermal delivery to a patient and the balance water, the percentages being by weight. Preferably, said water soluble polymer is polyvinylpyrrolidone, agar, agarose or a water soluble cellulose derivative, a preferred embodiment being polyvinylpyrrolidone. The polyvinylalcohol preferably has a molecular weight of from about 100,000 to about 150,000 and the polyvinylpyrrolidone preferably has a molecular weight of from about 20,000 to about 60,000. The polyvinylalcohol preferably has a molecular weight of from about 100,000 to about 150,000.

In a separate embodiment, a polymeric diffusion matrix in cured form suitable for providing protection to a burned or wounded patient is provided which comprises in the cured state from about 2 to about 55% glycerol, from about 4 to about 30% polyvinylalcohol, from about 2 to about 20% water soluble polymer with hydration sites which in combination with the remaining ingredients yields a matrix capable of sustained release of a drug dispersed therein, and the balance water, the percentages being by weight. Preferably said water soluble polymer is polyvinylpyrrolidone, agar, agarose, and a water soluble cellulose derivative, the preferred embodiment being polyvinylpyrrolidone. The polyvinylalcohol preferably has a molecular weight of from about 100,000 to about 150,000 and the polyvinylpyrrolidone preferably has a molecular weight of from about 20,000 to about 60,000. Preferably the ratio of polyvinylalcohol to polyvinylpyrrolidone is from about 2:1 to about 3:2. At least one topical drug may be incorporated in said matrix.

DETAILED DESCRIPTION OF THE INVENTION

Figure 1:
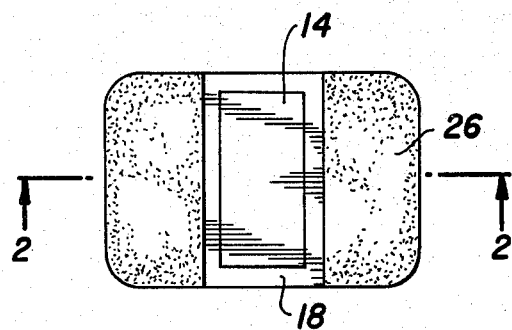
FIG. 1 shows a plan view of a bandage having incorporated therein the drug-containing polymeric diffusion matrix of the present invention.

According to the present invention, a polymeric diffusion matrix is provided comprising, on a weight basis, from about 2 to about 60% glycerol, from about 2 to about 15% polyvinylalcohol, from about 2 to about 10% water soluble polymer with hydration sites which is compatible with the remainder of the ingredients of the diffusion matrix to permit the sustained release of a drug, the balance being water. This water soluble polymer complements the polyvinylalcohol by providing retention of shape of the desired diffusion matrix. As such water soluble polymer with hydration sites suitable for the present invention may be mentioned agar, agarose, polyvinylpyrrolidone and water soluble derivatives. The matrix may further contain a therapeutically effective amount of one or more drugs suitable for topical or transdermal application to a patient, thus forming a drug delivery device.

When the present polymeric diffusion matrix is used as a burn matrix, the matrix is preferably in a cured state. By cured, it is meant that the polymeric diffusion matrix contains little or no excess water used in forming the matrix. As shown below, the diffusion matrix is formed by mixing together the glycerol, polyvinylalcohol, water soluble polymer with hydration sites and water to obtain a homogeneous mixture which is cast into sheets of the matrix. In order to allow casting of the mixture, it is sometimes necessary to use an excess amount of water. Immediately after casting, the polymeric matrix is in an "uncured" state. The excess water may then be permitted to evaporate. When substantially all of the excess water has evaporated, the polymeric matrix is in a "cured" state. As a result of the evaporation of the water, which generally requires from about 1 to about 18 hours, the thickness of the diffusion matrix is reduced, or a "collapsed" matrix is obtained.

In a first embodiment, the present invention provides a diffusion matrix for the application of drugs to a patient (drug delivery matrix). In another aspect of the present invention, the transdermal or topical application of drugs is contemplated via the diffusion matrix. The diffusion matrix of the present invention provides a steady release of the drug to the patient over an extended period, typically 24 hours.

In its uncured state, the polymeric diffusion matrix comprises, preferably, from about 2 to about 20% glycerol, from about 2 to about 15% polyvinylalcohol, from about 2 to about 10% polyvinylpyrrolidone, and the balance water, all percentages being by weight. Agar, agarose, water soluble cellulose derivatives or other compatible substances may replace all or part of the polyvinylpyrrolidone.

In the uncured matrix, the glycerol is present in an amount of from about 2 to 60%, preferably from about 2 to about 20%, by weight. When trinitroglycerol is the drug to be applied, the amount of glycerol preferably should be within the range of from about 35 to 60%.

Preferably, the glycerol has a minimum specific gravity of 1.23 g/ml.

The polyvinylalcohol is present in the uncured matrix in an amount of from about 2 to about 15%, preferably from about 4 to about 9% by weight. Preferably, the polyvinylalcohol has a molecular weight of at least about 70,000. Most preferably, the molecular weight is from about 100,000 to about 150,000.

The water soluble polymer with hydration sites is present in the uncured matrix in am amount of from about 2 to about 10%, preferably from about 2 to about 5%, by weight. In a preferred embodiment, polyvinylpyrrolidone is used as the water soluble polymer. The molecular weight for the polyvinylpyrrolidone should be selected to maintain water solubility. In general, this molecular weight should be within the range of from about 20,000 to about 60,000, preferably from about 35,000 to about 50,000. The polyvinylpyrrolidone may be replaced by other ingredients which permit sustained release. e.g. agar in an amount of from about 2% to about 6% by weight may be used.

The balance of the matrix comprises essentially water.

In its cured state, the polymeric diffusion matrix comprises, from about 2 to about 55%, preferably from about 4 to about 35% glycerol, from about 4 to about 30%, preferably from about 8 to about 20% polyvinylalcohol; from about 2 to about 20%, preferably from about 4 to about 10% a water soluble polymer having hydration sites, preferably polyvinylpyrrolidone, and the balance water, all percentages being by weight. The molecular weight ranges for the polyvinylalcohol and polyvinylpyrrolidone are the same for cured and uncured diffusion matrices. The cured matrix has a density of about 1.2 g/ml. It is noted that the weight ratio of glycerol to water in the cured matrix is about 0.6–1.8:1, preferably about 1:1. The cured matrix shows little swelling when immersed in water and will not dissolve in water at room temperature. However, if the water is heated to boiling, the diffusion matrix will dissolve.

At least one drug is dispersed throughout the diffusion matrix when the diffusion matrix is used as a drug delivery device. The type of drug which may be dispersed in the diffusion matrix of the present invention includes any drug which is capable of being transdermally or topically administered to a patient. With the sustained release of the drug at a relatively steady rate over a prolonged period, typically 24 hours, the patient is provided with the benefit of a steady application of the drug over the prolonged period. As examples of drugs which are suitable for inclusion in the diffusion matrix of the present invention there may be mentioned the following: alpha-[1(methylamino)ethyl1-benzene methanol, which is useful as an adrenergic (bronchodilator); N-phenyl-N-]1-(2-phenylethyl)-4-piperidinyll propanamide, useful as a narcotic analgesic; 6-chloro-3,4-dihydro-2H-1,2,4-benzothiadiazine-7-sulfonamide 1,1-dioxide, useful as a diuretic; 2-diphenylmethoxy-N,N-dimethylethanamine, useful as an antihistamine; and an estrogen. Other useful drugs include: antimicrobial agents such as penicillin, tetracycline, oxytetracycline, chlortetracycline, chloramphenicol, and sulfonamides, sedatives and hypnotics such as pentabarbital sodium, phenobarbital, secobarbital sodium, codeine, (α-bromoisovaleryl) urea, carbromal, and sodium phenobarbital; psychic energizers such as 3-(2-aminopropyl) indole acetate and 3-(2-aminobutyl) indole acetate; tranquilizers such as reserpine, chlorpromazine hydrochloride, and thiopropazate hydrochloride; hormones such as adrenocorticosteroids, for example, 6-methylprednisolone; androgenic steroids, for example, methyltestosterone, and fluoxymesterone; estrogenic steroids, for example, estrone, estradiol and ethinyl estradiol; progestational steroids, for example, 17α-hydroxyprogesterone acetate, medroxyprogesterone acetate, 19-norprogesterone, and norethindrone; and thyroxine; antipyretics such as aspirin, salicylamide, and sodium salicylate; morphine and other narcotic analgesics; antidiabetics, e.g. insulin, antipasmodics such as atropine, methscopolamine bromide, methscopolamine bromide with phenobarbital; antimalarials such as the 4-aminoquinolines, 9-aminoquinolines, and pyrimethamine; and nutritional agents such as vitamins, essential amino acids, and essential fats. The above listing of drugs is merely exemplary of the transdermally applicable drugs. It is contemplated that any drug which may be transdermally applied is sutiable for use as the drug to be applied via the diffusion matrix in the present device.

It will be appreciated that the drug may be added to the above mixture not only in the form of the pure chemical compound, but also in admixture with other drugs which may be transdermally applied or with other ingredients which are not incompatible with the desired objective of transdermally administering the drug to a patient. Thus, simple pharmacologically acceptable derivatives of the drugs such as ethers, esters, amides, acetals, salts, and the like may be used. In some cases such derivatives may actually be preferred.

The amount of the drug dispersed in the diffusion matrix can be varied in accordance with the desired dosage and the length of time the matrix is to remain on the skin. However, the amount of the drug included in the matrix should generally be in excess of the amount which is to be delivered to the patient. If the diffusion matrix is to be used for 24 hours, an approximate 10 fold excess of the drug should be included. For example, if it is desired to apply about 5 mg of trinitroglycerol to a patient over 24 hours, a roughly ten fold excess of the trinitroglycerol should be included in the diffusion matrix. Accordingly, from 40 to 60 mg is considered a preferred amount to provide a 5 mg release of trinitroglycerol over a 24 hour period. Quite obviously, the optimum amount that should be included in the diffusion matrix will vary according to factors such as the period of release of the drug.

In a preferred embodiment, there is used trinitroglycerol or 1,2,3-propanetriol trinitrate or nitroglycerin, which is useful in coronary medicine as a vasodilator. It is preferred to add the trinitroglycerol in the form of lactose triturate, in view of the danger of explosion of trinitroglycerol. In addition, the ratio of lactose triturate to the water and glycerol should avoid proportions where the trinitroglycerol may separated and raise and explosion hazard. A preferred lactose triturate is a composition comprising 10% nitroglycerin and 90% beta-lactose.

In forming the trinitroglycerol-containing matrix, excess water is not required. Hence, this matrix comprises from about 35 to about 60%, preferably from about 45 to about 55% glycerol; from about 2 to about 15%, preferably from about 4 to about 9% polyvinylalcohol; from about 2 to about 10%, preferably from about 2 to about 5% polyvinylpyrrolidone, and the balance being essentially water, all percentages being by weight. The amount of water evaporated from the uncured matrix is negligible, hence, the higher percentage for the glycerol. For this matrix, the weight ratio of glycerol to total polymers is usually greater than 1, preferably from about 1.4 to 15:1.

The amount of trinitroglycerol which should be used is based upon a desired delivery of about 5 mg per patient over a 24 hour period. The diffusion matrix drug delivery system of the present invention to deliver the 5 mg in the 24 hour period should contain about 40 to 60 mg of the trinitroglycerol. To reach this objective, the concentration of the trinitroglycerol in the diffusion matrix and the area of the diffusion matrix are factors to consider. In accordance with a preferred aspect of the present invention, from about 0.1 to about 4.0% by weight trinitroglycerol is included in the diffusion matrix. In a preferred aspect of the present invention, 80 ml of the solution is mixed with 20 gm of lactose triturate, with this mixture being mechanically stirred until it is homogenous. The resultant homogenous mixture is poured into forms preferably made of glass or stainless steel, these forms or templates producing a diffusion matrix having a thickness of about 3 to about 4 mm, in accordance with a preferred aspect of the present invention. This diffusion matrix is either cast or cut into pieces of the desired size. In a preferred aspect, squares of about one inch on each side, or about 6.5 cm$^2$, have been prepared or ease of application to the patient.

The following methods may be used for preparing the diffusion matrix of the present invention.

In a first method, the matrix is formed at atmospheric pressure. Water and glycerol are first mixed togethe. Since alkaline mixtures have relatively poor stability, the pH of the mixture is adjusted so that it is either neutral or slightly acidic, i.c., the pH ranging from about 6.5 to about 7.0. In a preferred embodiment, the pH is adjusted to within the above-mentioned range by adding sodium citrate and citric acid to the mixture.

The polyvinylalcohol an polyvinylpyrolidone are then added to the glycerol-water mixture at room temperature, with agitation. The mixture is heated to a temperature within the range of from about 90 to about 95° C. at atmospheric pressure to extend the polymers. The mixture is held at this temperature for about one hour. If desired, the mixture may be maintained at this temperature for a period of about 48 hours prior to the addition of the drug. Thus, the mixture is stable for a period of about 48 hours and may be kept for such a period before being mixed with the drug to be delivered to the patient. Thereafter, the mixture is cooled to 80° C. and stirred for an additional hour to remove bubbles therefrom. The drug to be applied to the patient is then added to the mixture, with thorough agitation. Once a homogenous mixture of the polymer solution and drug is obtained, the mixture is ready to be cast into sheets of the drug-containing diffusion matrix. In a preferred embodiment, the drug may be dissolved by agitation in a suitable solvent such as glycerin and water. The thus-obtained solution can be maintained at room temperature for prolonged periods without deterioration.

In a second method, water and glycerol are mixed, with the pH of the mixture adjusted to a desired value by adding suitable amounts of sodium citrate and citric acid. Thereafter, the polyvinylalcohol and polyvinylpyrolidone are added. The resulting mixture is then heated to a temperature of about 120° C. at a pressure of about 2 atmospheres absolute. The temperature is maintained for about 1 hour without any mechanical agitation. In a preferred embodiment, the heating may be performed in an autoclave. Since bubbles are not formed when the heating is conducted in an autoclave, such a procedure is preferred. Thereafter, the temperature is lowered to about 20 to about 80° C. whereupon the drug to be applied to the patient is added. After the drug has been homogenously dispersed in the liquid mixture, the mixture is poured into molds to form sheets of the drug-containing diffusion matrix.

In the above methods and for the case of trinitroglycerol and other drugs having similar limitations, the drug must be added and mixed thoroughly when the polymer mixture is in the liquid state. Furthermore, the mixture should be cast within about 30 minutes after the drug has been introduced into the polymer solution. This is important in order to avoid the setting of the polymer solution prior to casting.

The temperature at which the drug is to be added to the matrix solution depends on the stability of the drug. For example, trinitroglycerol begins to decompose at a temperature of above about 50° C. Accordingly, in preparing a trinitroglycerol-containing diffusion matrix, the matrix solution mixture is cooled to about 50°C., whereupon the trinitroglycerol is added. The drug-containing diffusion solution is then cast into molds to form sheets of the final product. In addition, for trinitroglycerol, the pH of the solution mixture should be kept slightly acidic, i.e., between 6.5 and 7.0 since trinitroglycerol is stabilized within this pH range.

A hydrophobic coating on a drug delivery matrix may be desired in the case of treating patients having wounds or burns. Silicone oil may be added in amounts of about 0.1 to 10% weight, based on the matrix, in the initial mixture of glycerol and water. Mineral oil or vegetable oil may substitute in whole or in part for the silicone oil. The oil serves to lower transdermal loss of water in the wounded or burned patient.

Dodecyl alcohol or sorbitan (Tween-20) or other detergents may be added in an amount of 0.1 to 10% by weight, based on the matrix, as a dispersing agent, if desired.

For drugs that are alcohol-soluble, it may be desirable to add the initial mixture of glycerol and water, ethanol or isopropanol in an amount of from 2 to 40% by weight, based on the matrix, to facilitate the preparation of a diffusion matrix for such alcohol-soluble drugs. In addition, ethanol and isopropanol, when added to the initial mixture, will provide a "collapsed" diffusion matrix, i.e., as the ethanol and isopropanol evaporate the diffusion matrix produced in accordance with the present invention will "collapse".

An absorption facilitator to insure skin penetration such as dimethylsulfoxide, decylmethylsulfoxide, or other penetration enhancers may be added.

If it is desired to increase the effective lifetime of the diffusion matrix, a drug reservoir may also be attached to the diffusion matrix. The diffusion matrix may also be used to help with local vasodilation to assist in the solution of physiological problems resulting from local circulatory difficiencies, for example, to promote circulation in the extremities of a geriatric patient.

The present drug delivery device comprises the drug-containing diffusion matrix and means for fastening the matrix to the skin of a patient. Such means can take various forms, such as an occlusive backing layer forming a kind of "bandage" with the diffusion matrix being held against the skin of a patient being treated. A polyethylene or Mylar tape is contemplated as one form of occlusive layer in accordance with the present invention. It can also take the form of an elastic band, such as a cloth band, a rubbery band or other material. Here, the diffusion matrix is placed directly on the skin and held in place by such elastic band which typically will be placed over the arm or wrist of the patient. An intermediate adhesive layer between the diffusion matrix and the skin capable of permitting the transdermal application of the drug can also be used.

As a preferred embodiment in the packaging of the present matrix, the drug-containing diffusion matrix is placed in a cavity provided in an inert backing material. Useful backing materials include metal foils such as aluminum foil, polyolefins such as polyethylene and polypropylene, polyesters such as Mylar (polyethylene terephthalate), polyamides such as Nylon, and the like. The drug-containing diffusion matrix can be poured in its molten state into the cavity and permitted to cool. An adhesive layer is provided on the backing material surrounding the cavity. To prevent air from coming into contact with the matrix, the adhesive layer and the matrix are sealed with a release layer. To use the device, the patient peels off the release layer and places the device in intimate contact with his skin. The exposed adhesive layer secures the device to the patient. Since a concentration gradient exists in a plane normal to the surface of the matrix and the patient's skin, this condition facilitates the drug to diffuse through the matrix into the patient's body. Thus, there is provided a device whereby a drug is delivered transdermally to a patient at a steady rate over a prolonged period of time.

Figure 2:
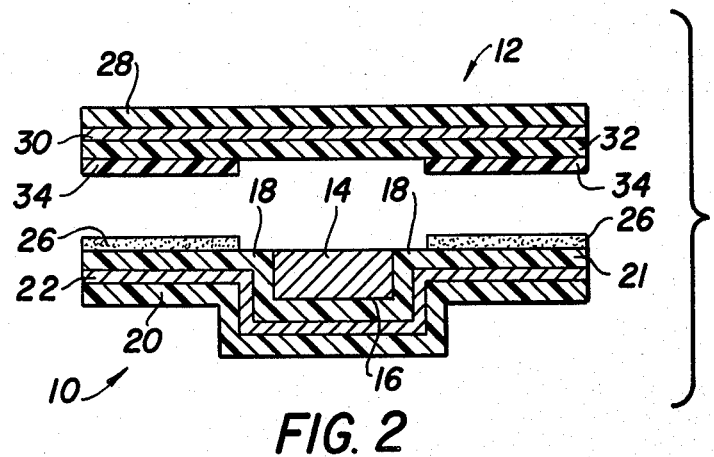
FIG. 2 illustrates a cross-sectional view along line 2—2' in FIG. 1

The contruction of a preferred embodiment for the packaging of the present invention is shown in further detail in FIGS. 1 and 2. As illustrated in the Figures, the package comprises a bandage having cover layer 12 and backing member 10. The diffusion matrix 14 having a drug (e.g. trinitroglycerol) dispersed therein is placed in cavity 16 in backing member 10. This diffusion matrix may be poured in its molten state into cavity 16 in backing member 10 and permitted to cure. Alternatively, the molten polymeric mixture (with or without a drug) is cast to form a thin sheet which is cut, after curing, into smaller sheets to fit the particular application of the matrix. Individual smaller sheats may then be placed in cavity 16 in backing member 10. The area 18 surrounding the matrix in the backing member 10 is heat sealed to prevent the matrix from being removed from the backing member. The backing member 10 is formed of a laminate comprising an outer layer 20 made of a polyester, such as polyethylene terephthalate, an intermediate layer 22 made of a metallic foil, e.g. aluminum foil, and an inner layer 24 made of a ionomer, such as Surlyn. A layer of pressure sensitive adhesive 26 is provided on the surface of the inner layer surrounding the heat sealed portion. It is noted that the adhesive does not cover the matrix.

The matrix is prevented from coming into contact with the atmosphere by placing cover layer 12 thereon, which seals the matrix. The cover layer is also formed of a laminate having the same construction as the backing layer, i.e. an outer layer 28 made of a polyester, e.g. polyethylene terephthalate; an intermediate layer 30 made of a metallic foil, e.g. aluminum foil; and an inner layer 32 of an ionomer, e.g. Surlyn. The surface of the inner layer coming into contact with the pressure sensitive adhesive 26 on the backing member 10 is coated with a release layer to permit easy removal of the cover layer.

To apply the drug to the patient, the cover layer is peeled off. The exposed matrix is then taped onto a suitable portion of the patient's body, e.g. arm or wrist, to allow the drug to diffuse thereinto.

In the preferred embodiment wherein trinitroglycerol is dispersed in the polymeric diffusion matrix, the molton matrix is cast into cavities provided in the backing member. The matrix is permitted to cure for a short period (e.g. about 10 minutes to about one hour) and is sealed by placing the cover layer over the backing member.

In another embodiment of the present invention, a polymeric matrix for application to a burned portion of a patient's body is provided (burn matrix). In this embodiment, the matrix comprises a water soluble polymer with hydration sites, polyvinylalcohol, glycerol and water. Examples of the water soluble polymer include polyvinylpyrrolidone, agar, agarose, water-soluble cellulose derivatives, and other compounds which are compatible with the remainder of the ingredients of the diffusion matrix of the invention to permit sustained release of a drug.

For a matrix in an uncured state, the water soluble polymer is present in an amount of from about 2 to about 10%, preferably from about 3 to about 8% by weight. For polyvinylpyrrolidone, which is a preferred water soluble polymer, it has a molecular weight of from about 25,000 to about 60,000, preferably from about 35,000 to about 50,000. The polyvinylalcohol is present in an amount of from about 2 to about 15%, preferably from about 6 to about 12% by weight. The polyvinylalcohol has a molecular weight of from about 100,000 to about 150,000, preferably from about 120,000 to about 135,000. The glycerol is present in an amount of from about 2 to about 20%, preferably from about 2 to about 18% by weight. Preferably, the glycerol is a 96% aqueous glycerol solution.

As a preferred embodiment, there is provided a polymeric diffusion matrix which comprises in its uncured state and on a weight basis: about 10.5% polyvinylalcohol (molecular weight 126,000); about 6% polyvinylpyrrolidone (molecular weight 40,000); about 15% glycerol; and the balance water.

The relative weight amounts of polyvinylalcohol to polyvinylpyrrolidone that have been considered range from about 3:1 to about 1:1. In actual practice, however, at a range of about 3:1, less than optimum results are obtained with the burn matrix swelling to an unacceptable degree, and at the ratio of 1:1 the burn matrix tends toward being soft and sticky Accordingly, in accordance with a preferred aspect of the present invention, it has been discovered that a weight range of polyvinylalcohol to polyvinylpyrrolidone should be between about 2:1 and about 3:2. The weight ratio of glycerol to total polymers for the burn matrix is usually less than 1, preferably about 0.5–1:1.

The amount of water which is to be utilized in the preparation of a burn matrix in accordance with the present invention in its generic aspect is related to the amount of glycerol which is used to make the burn matrix of the present invention. The amount of water by volume exceeds the amount of glycerol that is used in the initial mixture of ingredients. According to a preferred embodiment of the present invention, water is present in an amount of from about three to about seven times the amount of glycerol present in the initial mixture of ingredients. After the manufacture of the burn matrix of the present invention, the matrix is "cured" to eliminate most of the water, where water has been used in excess. The amount of time for the cure depends upon conditions such as the amount of excess water. In a preferred embodiment where 20 ml of glycerol is mixed with 100 ml water, the cure time is about 24 hours, yielding a burn matrix with an approximately equal amount of water and glycerol.

In order to prepare the burn matrix of the present invention, the water and glycerol are mixed together, preferably at a somewhat elevated temperature, e.g., 50° C. The polyvinylalcohol and the polyvinylpyrrolidone are added under agitation with the temperature being raised and with continued agitation until solution is effected. The temperature in one embodiment is raised to about 95° C. with solution being effected at that temperature. The resultant homogenous mixture is then poured onto forms which are typically of glass or stainless steel serving as templates to produce a burn matrix having a thickness of about 3 to about 4 mm. Where exccess water has been included in the burn matrix, the burn matrix is cured to permit elimination of the excess water. For example, where a 5:1 volume ratio of water to glycerol is used, the freshly prepared burn matrix is permitted to set for about 24 hours, resulting in a burn matrix having a thickness of about 1 to 2 mm. The preferred thickness for a "cured" burn matrix is from about 0.1 to about 2 mm.

The molten burn matrix is preferably cast to form a sheet of the matrix. After curing, the sheet is cut into smaller sheets having a suitable surface area. The smaller sheets can then be deposited on an appropriate backing layer. Alternatively, the molten burn matrix material can be poured onto a backing layer to form a sheet of the matrix in intimate contact with the backing layer. The backing layer can be made of laminates comprising a polyester outer layer, a metal foil intermediate layer, and a ionomer inner layer. The matrix/backing layer laminate can be wound to form a roll of the matrix or cut into smaller sheets of suitable size.

Where drugs are to be included in the burn matrix, they may be added, in the case of drugs soluble in the burn matrix, to the homogenous mixture prior to casting, or after curing of the matrix, by the physician or pharmacist at his direction shortly before the need for application arises, permitting a wider flexibility in topically applying a medicine to the patient. Generally, water insoluble drugs may be included in the burn matrix either through original incorporation into the mixture of water and glycerol or through subsequent application of the drug into the already prepared burn matrix. Where the drug is to be applied to a typical burn matrix of the invention having a thickness of about 2 mm, the drug may be painted onto a surface of the burn matrix or it may be applied through other means, such as an aerosol. A sufficient period of time, e.g., 4 hours, should be provided for the drug to diffuse through the burn matrix of the present invention. In order to provide an anesthetic effect, a water soluble anesthetic such as xylocaine may be applied through any of the above modes available for water soluble drugs. The amount of the water soluble drug that is to be dispersed in the burn matrix of the present invention should be in excess of the amount which is to be administered to the patient. An excess of 1:1 to 10 times the actual amount of drug which is to be administered to the patient should generally be used.

A water-soluble antibiotic to counter the possibility of infection should also be considered for inclusion in the burn matrix of the present invention. Because of the option of including the specifically desired antibiotic after the preparation of the burn matrix of the present invention, the individual physician is given great latitude in selecting the desired antiobiotic to take into account the particular needs of the specific patient being treated. As an example of a water soluble antibiotic which may be incorporated into the burn matrix of the present invention may be mentioned Penicillin VK.

Water insoluble materials may also be desirably included in the burn matrix of the present invention. Such materials are preferably introduced directly into the initial mixture of water and glycerol at the outset of the manufacturing process for making the burn matrix of the present invention. In accordance with one aspect of the invention, there is provided a zinc substance in an amount from about 0.4 to about 2% by weight based upon the final weight of the cured burn matrix of the present invention. Zinc chelates may be used as the zinc substance of this aspect of the present invention. In accordance with a further embodiment within the scope of the present invention about 0.4 to about 2% by weight zinc or silver sulfadiazine is incorporated into the burn matrix of the present invention for retarding Pseudomonas infections.

In making zinc or silver (or other water-insoluble containing) burn matrix of the present invention, the zinc or silver material is preferably added with a small amount of the glycerol. The amount of glycerol needed to make the suspension is subtracted from the amount of glycerol initially mixed with the water. A uniform suspension of the zinc or silver compound and glycerol is added together with the water and remainder of the glycerol, preferably as the last stage prior to casting.

In addition to local anesthetics and antibiotics which can be applied to or incorporated into the burn matrix of the present invention, other topical medicines may also be applied to or incorporated in the burn matrix. Examples of useful topical drugs include fungicides, bactericides, antimicoplasma (E. coliplasma), analgesics and local anesthetics.

The amount of drug which can be incorporated into the burn matrix is up to about 1% by weight of the burn matrix. By incorporated, it is meant that the drug is added to the polymer mixture before casting. As to the amount of drug which can be painted onto the suface of the matrix this varies in accordance with the drug applied.

If desired, a hydrophobic casting may be desired in the burn matrix of the present invention. Silicone oil may be added in amounts of about 0.1 to 10% by weight, based on the matrix in the initial mixture of glycerol and water. Mineral oil or vegetable oil may substitute in part or whole for the silicone oil, which lowers the transdermal loss of water in the patient.

The burn matrix in accordance with the present invention is a flexible and transparent polymer which is suited for being applied directly to a burned portion of the patient being treated for most parts of the body. After hydration, the burn matrix is highly flexible and will adhere mildly to the skin. The degree of adherence is sufficient to hold the burn matrix in place but not enough to injure the patient's skin when it is removed. It is contemplated that the burn matrix should be replaced periodically, typically at 24 hour or longer intervals.

The burn matrix of the present invention may be stored for prolonged periods, particularly when placed in a sealed container.

The cured matrix of the present invention can be used in agricultural applications. In such instances, pesticides (for controlling microbial and other disease causing organisms), herbicides, insecticides and insect repellents may be incorporated in the matrix. The matrix can be applied to the animal or plant topically or parenterally (i.e. by implantation).

The method of administration of this invention is suitable also for adaptation to buccal and especially to sublingual administration. Because of the much higher rate of absorption through the mucosa by that route, much shorter periods of administration are required.

The invention is illustrated by the following nonlimiting Examples:

EXAMPLE I 45 ml glycerol and 45 ml water together with 1% by weight sodium citrate are mixed together and the pH adjusted to 7 through addition of citric acid. This mixture is heated to 90° C.; after reaching at least 70° C. there are slowly added 7 gm polyvinyl alcohol (PVA 100% hydrolyzed, molecular weight 115,000) and 5 gm polyvinylpyrrolidone (mw 40,000). The mixture is stirred at 90° C. until solution is effected, which may take about 10 minutes, it being appreciated that with larger quantities, a considerably longer period of time may be needed. 80 ml of this solution is then mixed with 20 gm lactose triturate (10% nitroglycerin and 90% lactose), this mixture then being mechanically stirred until homogenous. The homogenous mixture is then poured into forms made of glass or stainless steel which serve as templates to produce a diffusion matrix having a thickness of about 3 to 4 mm. This diffusion matrix is then cut into square pieces of about 1 inch on each side, i.e., to provide a total surface area of about 6.5 cm$^2$.

EXAMPLE II

Example I is repeated with the exception that 3 gm of agar is used instead of the polyvinylpyrrolidone. Also included in the mixture is 1% by weight calcium chloride.

EXAMPLE III

The diffusion matrix of Example I is applied to a patient by placing it against the wrist, shoulder or other sites of the patient.

EXAMPLE IV

The diffusion matrix of Example I is applied to a patient by first attaching the diffusion matrix to a MYLAR or polyechylene backing layer. This occlusive backing layer is provided with an adhesive whereby the diffusion matrix is held in contact with the skin as part of this "bandage".

EXAMPLE V-X

By substituting an appropriate amount of the following chemicals, in place of the lactose triturate, otherwise following the procedure of Example I, a diffusion matrix is obtained:

| EXAMPLE | COMPOUND | USE |
|---|---|---|
| V | Alpha-[1(methylamino)-ethyl] benzene methanol | adrenergic (bronchodilator) |
| VI | N—phenyl-N—[1-(2-phenylethyl)-4-piperidinyl]propamide | narcotic analgesic |
| VII | 6-chloro-3,4-dihydro-2H,1,2,4-benzothiadiazine-7-sulfonamide 1,1-dioxide | diuretic |
| VIII | 2-diphenylmethoxy-N,N—dimethyl-ethanamine | antihistamine |
| IX | estra-1,3,5(10)triene-3-,17beta-diol | estrogenic |
| X | 5-ethyl-5-phenyl-2,4,6(1H,3H,5H)-pyrimidinetrione | anticonvulsant, hypnotic, sedative |

EXAMPLE XI 948 g of 96% glycerol and 644 g of water are mixed together. 27 g of sodium citrate, 159 g of polyvinyl alcohol (molecular weight 115,000), 93 g of polyvinylpyrrolidone (molecular weight 40,000) are dissolved in the glycerol/water mixture by continuous stirring and maintaining at a temperature of about 90° C.

In a separate container, 600 g of nitroglycerin triturate (10% nitroglycerin and 90% lactose) is dissolved in 315 g glycerol and 214 g water with agitation at room temperature.

When the polymers have gone into solution, the nitroglycerin triturate dispersion is poured therein. The mixture is mixed thoroughly at a temperature range of between 50° and 55° C. to form a homogenous mixture. The container is kept covered.

The homogenous mixture is poured into forms made of glass or stainless steel which serve as templates to produce a drug-containing diffusion matrix having a thickness of about 3 to 4 mm. This diffusion matrix is then cut into square pieces of about 1 inch on each side, i.e. to provide a total surface area of about 6.5 cm$^2$.

EXAMPLE XII 100 ml and 20 ml glycerol are mixed together and heated to about 50° C. 8 gm polyvinylalcohol (molecular weight 126,000, 100% hydrolyzed) is slowly added while the preparation is undergoing rapid agitation. After the polyvinylalcohol is uniformly dispersed, 5 gm polyvinylpyrrolidone (molecular weight 40,000) is added with continued stirring. The preparation is then heated to about 95° C. until solution is effected. At this point, the preparation may be cast onto a flat sheet so that it can harden.

The homogenous mixture is poured onto a stainless steel plate resulting in an uncured burn matrix having a thickness of about 3 to 4 mm. The burn matrix is cured by letting water evaporate for about 24 hours, leaving a cured burn matrix having a thickness of about 1 to about 2 mm.

The burn matrix has the following compositions:

| | % by weight | |
|---|---|---|
| Ingredients | uncured | cured |
| glycerol | 17.9 | 34.6 |
| polyvinylalcohol | 5.8 | 11.3 |
| polyvinylpyrrolidone | 3.6 | 7.0 |
| water | 72.7 | 47.0 |

EXAMPLE XIII

A piece of the cured burn matrix of Example XII is placed on a test system of 10% aqueous gelatin cast into a petri plate, to serve as a model for testing the burn matrix. On this model, it was found that the burn matrix of the present invention does not appreciably swell but does permit a small amount of water evaporation and further permits the exchange of some gases by diffusion processes across the perpendicular dimension of the burn matrix. The burn matrix of the present invention retards the loss of water vapor from a 10% gelatin preparation by approximately a factor of 10.

EXAMPLE XIV

A one inch square piece of the cured burn matrix of Example XII is used as a model for preparing a burn matrix with water soluble medicinal additives. Painted onto one side of the burn matrix of Example I is 10 mg of Xylocaine. After painting the Xyocaine onto the burn matrix, the burn matrix is permitted to stand for about 4 hours, resulting in a burn matrix having diffused therein the Xylocaine.

EXAMPLE XV

In place of the Xylocaine of Example XIV, 30 mg of Penicillin VK is applied to the burn matrix, resulting in a burn matrix having antibiotic properties over the 24 hour period desired for the life of the burn matrix.

EXAMPLE XVI

Example XIV is repeated, except that in addition to the Xylocaine, there is also simultaneously painted onto the burn matrix 30 mg Penicillin VK. The resultant burn matrix provides both antibiotic protection against infection and relief from pain over an extended period, due to the slow release of the Xylocaine over a prolonged period.

EXAMPLE XVII

The procedure of Example XII is repeated, with the following variations: 18 ml instead of 20 ml glycerol is used. In addition, sufficient zinc sulfadiazine to make up 1% by weight of the final cured burn matrix is suspended in 2 ml glycerol. This suspension is added to the mixture of other ingredients as the last step prior to pouring onto the stainless steel plate.

The resultant cured burn matrix provides the additional advantage of protecting the burn victim over an extended period against Pseudomonas infection. In place of zinc sulfadiazine, silver sulfadiazine may be used.

EXAMPLE XVIII

The procedure of Example XVII is repeated except that the zinc sulfadiazine is replaced by 20 mg of Cephalosporin, resulting in a burn matrix having antibiotic properties.

EXAMPLE XIX

Male dogs are anesthetized with sodium pentothal. Through surgical incisions, catheters are positioned in the femoral veins of each hind leg and in the abdominal aorta. Flow gauges are placed on the internal iliacs of both hind limbs. On a well-shaved area of the medial surface of the left thigh, a nitroglycerin containing polymer matrix obtained in Example I is taped in place and remains undisturbed for 4 hours. The right hind limb receives no matrix or treatment of any kind. After application of the matrix, blood samples (5 ml) are taken from the catheters in each of the femoral veins and from that in the abdominal aorta at 15, 30, 60, 120, 180 and 240 minutes. Once drawn, the blood samples are put in ice, centrifuged (for 10 minutes) at 0° C., and 2 ml plasma is transferred to a silanized (with an alkylated silicone oil) glass tube. To each tube, 5 ml n-pentane is also added and the nitroglycerin is extracted for 1 hour with gentle shaking at 0° C. The pentane phase is then transferred to a 5 ml capacity Recti-Vial™ and evaporated to near dryness. The residue is then dissolved in 30 microliters benzene containing 2 nanograms para-nitroanisole used as the external standard. 1.0 to 50.0 microliters of this solution is then injected for nitroglycerin quantitation using GLC-Electron Capture Detection. (A Hewlett-Packard 4610A Gas chromatograph equipped with a $^{63}$Ni-electron capture detector.) Separation is achieved on a 4 foot × 3 mm I.D. glass column packed with 10% SE-30 on 100/120 mesh GASCHROM Q™. The column is maintained at 140° C. while the injection-port temperature is 170° C. and detector temperature: 220° C. A nitroglycerin calibration curve is constructed from the analyses of nitroglycerin spiked blank plasma.

The results from the above test runs, summarized in Table 1, show dramatically that nitroglycerin is absorbed transepidermally from the matrix over the entire 4 hour period. Also, the levels attained in the venous blood draining the limb containing the matrix are grossly proportional to the matrix surface area in contact with the skin.

From the results of the studies here discussed, it is evident that transepidermal nitroglycerin absorption has occurred from the matrix to blood.

The nitroglycerin absorption rate appears to be fairly constant from 30–240 minutes as depicted by the essentially non-varying arterial nitroglycerin plasma levels.

TABLE I

| MATRIX SIZE - | 2" × 3" | 2" × 1" | 1" × 1" |
|---|---|---|---|
| STUDY No. | 1 | 2 | 3 |
| SAMPLE | nanograms nitroglycerin per ml. plasma | | |
| ARTERIAL - 15 min. | 0.68 | 0.14 | 0.27 |
| ARTERIAL - 30 min. | 0.57 | 0.15 | 0.53 |
| ARTERIAL - 60 min. | 0.73 | 0.15 | — |
| ARTERIAL - 120 min. | 0.85 | 0.49 | 0.36 |
| ARTERIAL - 180 min. | 1.29 | 0.68 | 0.50 |
| ARTERIAL - 240 min. | 1.26 | 0.21 | 0.30 |
| EXPERIMENTAL VENOUS - 15 min. | 0.95 | 5.70 | 0.40 |
| EXPERIMENTAL VENOUS - 30 min. | 0.51 | 8.31 | 0.32 |
| EXPERIMENTAL VENOUS - 60 min. | 15.3 | 11.4 | 0.52 |
| EXPERIMENTAL VENOUS - 120 min. | 26.9 | 7.63 | 0.75 |
| EXPERIMENTAL VENOUS - 180 min. | 32.9 | 13.7 | 0.57 |
| EXPERIMENTAL VENOUS - 240 min. | 32.0 | 5.55 | 0.23 |
| CONTROL VENOUS - 15 min. | 0.44 | 9.18 | 0.09 |
| CONTROL VENOUS - 30 min. | 0.61 | 21.6 | 0.15 |
| CONTROL VENOUS - 60 min. | 7.40 | 4.51 | 0.28 |
| CONTROL VENOUS - 120 min. | 2.33 | 13.0 | 0.42 |
| CONTROL VENOUS - 180 min. | 9.87 | 14.5 | 0.39 |
| CONTROL VENOUS - 240 min. | 13.9 | 4.10 | 0.23 |

EXAMPLE XX

Five male mongrel dogs, free of disease, are anesthetized with sodium pentobarbital. Under a septic surgical procedure, a catheter is inserted into the right artrium via the jugular vein for the removal of blood samples from the right heart. An arterial catheter is placed in the right carotid artery for the continuous recording of arterial blood pressure. Both catheters are exteriorized at the back of the neck.

The animals are allowed to recover from the anesthetic and are studied 24 hours later in the fasted, conscious state while resting comfortably in a supporting harness.

Each animal is allowed to become familiar with the laboratory surroundings and when completely acclimated, a 20 ml reference blood sample is obtained from the right heart catheter. A 1.0"×1.0" square of the nitroglycerin containing polymer matrix obtained in Example I is then applied to a well shaved area of the right lateral chest wall. The matrix is held securely in place with surgical tape. After application of the polymer matrix, 5.0 ml blood samples are obtained at 15 min, 30 min, 45 min, 1 hr, 2 hr, 3 hr, 4 hr, 5 hr, 6 hr, 7 hr, 8 hr, 9 hr, 10 hr, 11 hr, 12 hr, 14 hr, 16 hr, 18 hr, 20 hr, 22 hr and 24 hr. The animals are conscious and unrestrained during the entire 24 hour period of sampling. At no time do the animals display any unfavorable effects due to the transcutaneous administration of nitroglycerin.

Immediately after drawing, blood samples are put in ice and transferred to a walk-in refrigerator and centrifuged for 10 minutes at 0° C. A 2 ml aliquot of plasma is taken from each specimen and transferred to individual silanized (with an alkylated silicon oil) glass tubes. A 5 ml volume of n-pentane is added to each tube and the nitroglycerin is extracted for 60 minutes with gentle shaking at 0° C. The pentane phase is transferred to a 5 ml capacity Reacti-Vial and evaporated to near dryness. The residue is dissolved in 30 microliters of benzene containing 2 nanograms of para-nitro-anisole used as the external standard. A 1.0 to 5.0 microliter aliquot of this solution is injected for nitroglycerin quantitation using GLC-Electr 1 Capture Detection (Hewlett-Packard 4610A Gas Chromatograph equipped with a $^{63}$Ni-electron capture detector.) Separation is achieved on a 4 foot × 3 mm I.D. glass column packed with 10% SE-30 on 100/120 mesh GAS-CHROM Q$^{TM}$. The column is maintained at 140° C. While the injection-port temperature is 170° C., and detector temperature 220° C. A nitroglycerin calibration curve is constructed from the analyses of nitroglycerin-spiked blank plasma.

Table 2 summarizes the plasma nitroglycerin data from the dogs. At each time point the mean ± the standard deviation is listed in the Table.

TABLE 2

| HOURS POST APPLICATION | ng nitroglycerin/ml. plasma | | | | | | |
|---|---|---|---|---|---|---|---|
| | DOG #1 | DOG #2 | DOG #3 | DOG #4 | DOG #5 | 5 DOGS | +/− S.D. |
| 0.25 | 0.11 | 0.39 | — | 0.37 | — | 0.29 | 0.16 |
| 0.50 | 0.08 | 0.28 | 0.02 | 0.16 | 0.16 | 0.14 | 0.098 |
| 0.75 | 0.08 | 0.29 | 0.02 | 0.14 | 0.19 | 0.14 | 0.10 |
| 1.00 | 0.23 | 0.19 | 0.15 | 0.10 | 0.36 | 0.21 | 0.099 |
| 2.00 | 0.22 | 0.57 | 0.02 | 0.22 | 0.27 | 0.26 | 0.20 |
| 3.00 | 2.06 | 0.38 | 0.04 | 0.88 | 0.17 | 0.71 | 0.82 |
| 4.00 | 0.52 | 0.81 | 0.11 | 0.28 | 0.26 | 0.40 | 0.27 |
| 5.00 | 0.22 | 1.00 | 0.28 | 0.17 | 0.11 | 0.36 | 0.37 |
| 6.00 | 0.23 | 0.63 | 0.24 | 0.55 | 0.88 | 0.51 | 0.28 |
| 7.00 | 0.93 | 0.70 | 0.45 | 0.34 | 1.23 | 0.73 | 0.36 |
| 8.00 | 0.16 | 2.39 | 0.70 | 0.42 | 0.45 | 0.82 | 0.90 |
| 9.00 | 0.22 | 0.59 | 0.32 | 0.34 | 0.10 | 0.31 | 0.18 |
| 10.00 | 0.11 | 0.83 | 0.59 | 0.31 | 0.66 | 0.50 | 0.29 |
| 11.00 | 0.07 | 0.77 | 0.13 | 0.35 | 0.50 | 0.36 | 0.28 |
| 12.00 | 0.35 | 0.55 | 0.37 | 0.29 | 0.12 | 0.34 | 0.15 |
| 14.00 | 0.04 | 0.39 | 0.18 | 0.17 | 0.20 | 0.20 | 0.13 |
| 16.00 | 0.07 | 0.41 | 0.28 | 0.57 | 0.32 | 0.38 | 0.17 |
| 18.00 | 0.26 | 1.17 | 0.32 | 0.29 | 0.39 | 0.49 | 0.39 |
| 20.00 | 0.34 | 0.41 | 0.52 | 0.33 | 0.24 | 0.31 | 0.11 |
| 22.00 | 0.20 | 1.11 | 0.66 | — | — | 0.66 | 0.46 |
| 24.00 | 0.27 | 0.43 | — | — | — | 0.35 | 0.11 |

From these results, it is evident that transcutaneous nitroglycerin absorption does occur, and does so at a constant and continuous rate so as to achieve a plateau plasma nitroglycerin level ranging from about average values of 0.3–0.6 nitroglycerin /ml. plasma. The data also show that the temporal limits of the nitroglycerin matrix have not been exceeded, or for that matter, have not been approached during the 24 hour experimental period. In each case, the apparent plateau nitroglycerin level shows no evidence of decreasing, either before or at the 24 hour experimental time limit.

What is claimed is:

1. A transdermal drug delivery vehicle, which contains a sedative, chosen from the group consisting of pentabarbital sodium, phenobarbital, secobarbital, sodium, codeine, (α-bromoisovaleryl)urea, carbromal and sodium phenobarbital, capable of being delivered transdermally over a prolonged period of time through the unbroken skin of a patient, in the form of a shape-retaining matrix for direct application to the skin of a patient in need of the sedative to be delivered, said matrix comprising from about 2 to about 60% glycerol, from about 2 to about 15% polyvinylalcohol molecular weight of from about 100,00 to about 150,000, from about 2 to about 10% polyvinylpyrrolidone molecular weight of from about 20,000 to about 60,000 and the balance water, cast or molded from hot solution thereof.

2. A transdermal drug delivery vehicle according to claim 1 in combination with an occlusive backing layer for holding the matrix against the skin of the patient being treated.

3. A transdermal drug delivery vehicle according to claim 1 wherein the matrix is placed in a cavity in an inert backing material.

4. A transdermal drug delivery vehicle according to claim 1 wherein the matrix is molded in situ in the cavity.

5. A transdermal drug delivery vehicle according to claim 1 wherein the sedative is phenobarbital.

6. A method of delivering a systemically active sedative to a patient over a prolonged period of time at a steady rate which comprises applying to the skin of said patient a transdermal drug delivery vehicle, which contains a sedative capable of being delivered transdermally over a prolonged period of time through the unbroken skin of a patient, said sedative chosen from the group consisting of pentabarbital sodium, phenobarbital, secobarbital sodium, codeine, (α-bromoisovaleryl)urea, carbromal and sodium phenobarbital, in the form of a shape-retaining matrix for direct application to the skin of a patient in need of the sedative to be delivered, said matrix comprising from about 2 to about 60% glycerol, from about 2 to about 15% polyvinyl alcohol molecular weight of from about 100,000 to about 150,000, from about 2 to about 10% polyvinylpyrrolidone molecular weight of from about 20,000 to about 60,000 and the balance water, cast or molded from hot solution thereof.

7. A method according to claim 6 wherein the transdermal drug delivery vehicle is attached to an occulsive backing layer for holding the matrix against the skin of the patient being treated.

8. A method according to claim 6 wherein the matrix is located in a cavity in an inert backing material.

9. A method according to claim 6 wherein the sedative is phenobarbital.

* * * * *